United States Patent [19]

Bodine

[11] Patent Number: 4,660,550
[45] Date of Patent: Apr. 28, 1987

[54] ARTICULATED HAND SPLINT WITH MULTIPLE PIVOT POINTS

[76] Inventor: Rudolph H. Bodine, 6074 107th Ave., Pinellas Park, Fla. 33565

[21] Appl. No.: 759,566

[22] Filed: Jul. 26, 1985

[51] Int. Cl.[4] .............................. A61F 5/04; A61F 5/10
[52] U.S. Cl. .......................................... 128/77; 128/88
[58] Field of Search .............................. 128/77, 88, 26

[56] References Cited

U.S. PATENT DOCUMENTS

| 161,323 | 3/1875 | Brown et al. ......................... 128/88 |
| 1,177,398 | 3/1916 | Dorang .................................. 128/88 |
| 3,707,963 | 1/1973 | Keropian ............................... 128/77 |
| 3,769,970 | 11/1973 | Swanson ................................ 128/77 |

FOREIGN PATENT DOCUMENTS

| 294027 | 8/1915 | Fed. Rep. of Germany ........ 128/77 |
| 313177 | 7/1919 | Fed. Rep. of Germany ........ 128/77 |
| 20724 | 4/1919 | France .................................. 128/26 |
| 112265 | 4/1918 | United Kingdom .................. 128/77 |

*Primary Examiner*—Edgar S. Burr
*Assistant Examiner*—Tonya Lamb
*Attorney, Agent, or Firm*—Herbert W. Larson; Joseph C. Mason

[57] ABSTRACT

Articulated hand splint having an arm support frame and a hand grip housing connected together with a transition bracket. Two or more pivot points in the bracket provide opportunity for a therapist to set the hand in any of two or more different positions.

9 Claims, 9 Drawing Figures

ARTICULATED HAND SPLINT WITH MULTIPLE PIVOT POINTS

DESCRIPTION

1. Technical Fields

This invention relates to hand splints. More particularly, it refers to an articulated hand splint for use on persons with spasticity, especially if caused by brain trauma.

2. Background Art

Hand splints of various types are well known in the prior art. An example of an early patented splint is set forth in U.S. Pat. No. 1,177,398. This splint was designed to be movable in one dimension so that it could be pre-set for use on either a right or left arm. It is not adaptable to spastic patients. Another early patented splint is set forth in U.S. Pat. No. 161,323. This is a fracture support splint that can be pre-set by movement of the parts laterally or vertically. It too is not adaptable for use with spastic patients. A more recent articulated hand brace is shown in U.S. Pat. No. 3,707,963. Although this brace is helpful to spastic patents it suffers from a difficulty of being hard to place on a hand and not easily removable. The frequent removal of such a brace is important both for the comfort of the patient and the prevention of sores caused by rubbing and general pressure contact. A brace device that can be pre-set for various angles desired by a treating occupational therapist and still be easily attached and removed from the patient's arm is needed.

SUMMARY OF THE INVENTION

I have designed an articulated hand splint that is movable in three directions by an occupational therapist so as to position a paralyzed hand in alignment with the forearm and away from a deflected position. At the same time, the splint is designed to allow easy removal and reapplication to the patient's forearm and hand.

My articulated hand splint comprises an arm support frame and a hand grip housing connected together with a transition bracket containing three pivot points allowing up and down, side to side and a rotating movement of the hand grip housing with respect to the arm support frame attached to a forearm. A hand grip in the hand grip housing prevents hand deflection.

BRIEF DESCRIPTION OF THE DRAWINGS

The present invention may be best understood by those of ordinary skill in the art by reference to the following detailed description when considered in conjunction with the accompanying drawings in which.

DESCRIPTION OF THE PREFERRED EMBODIMENT

The articulated hand splint 10 is made of three principal parts, namely, an arm support frame 12, a hand grip housing 14 and a transition bracket 16 joining the arm support frame 12 and hand grip housing 14.

Figure 1:
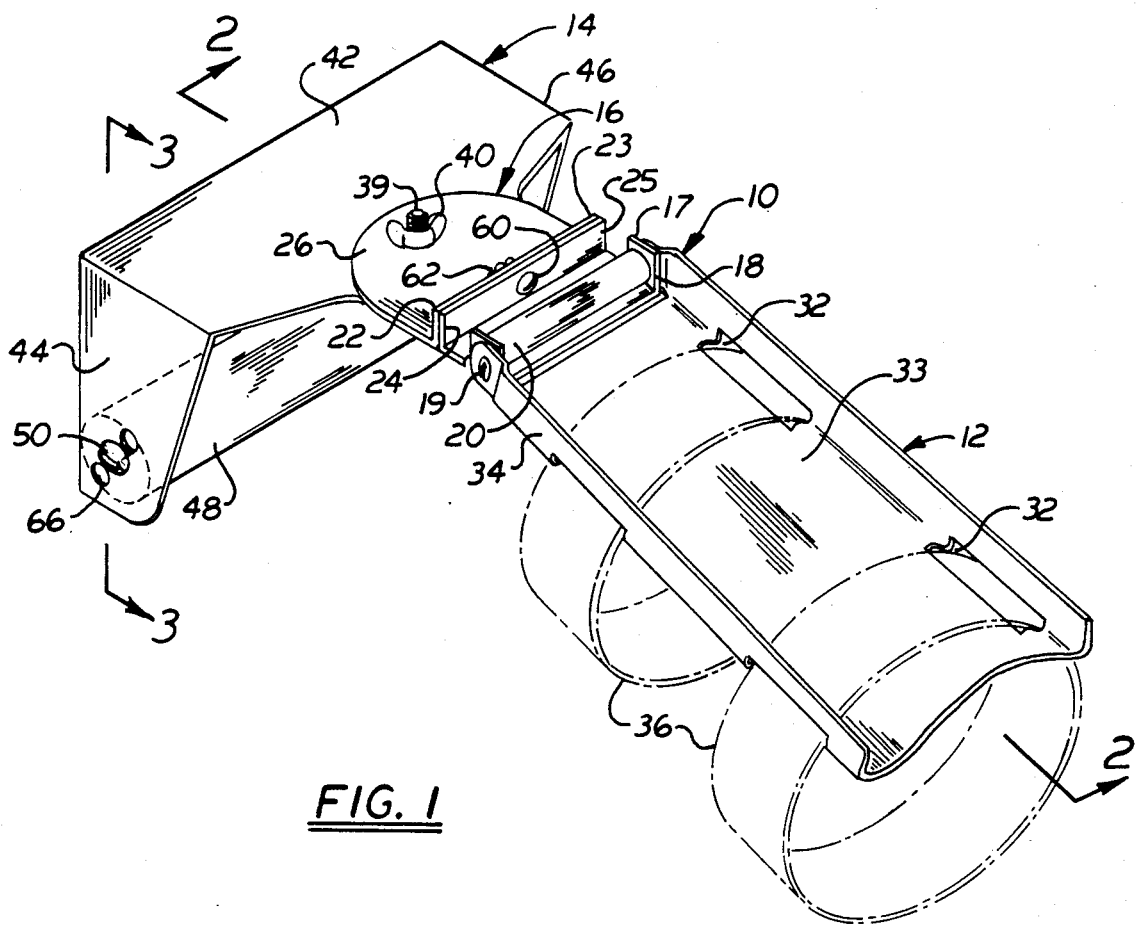
FIG. 1 is a perspective view of an articulated hand splint movable in three directions.
Figure 2:
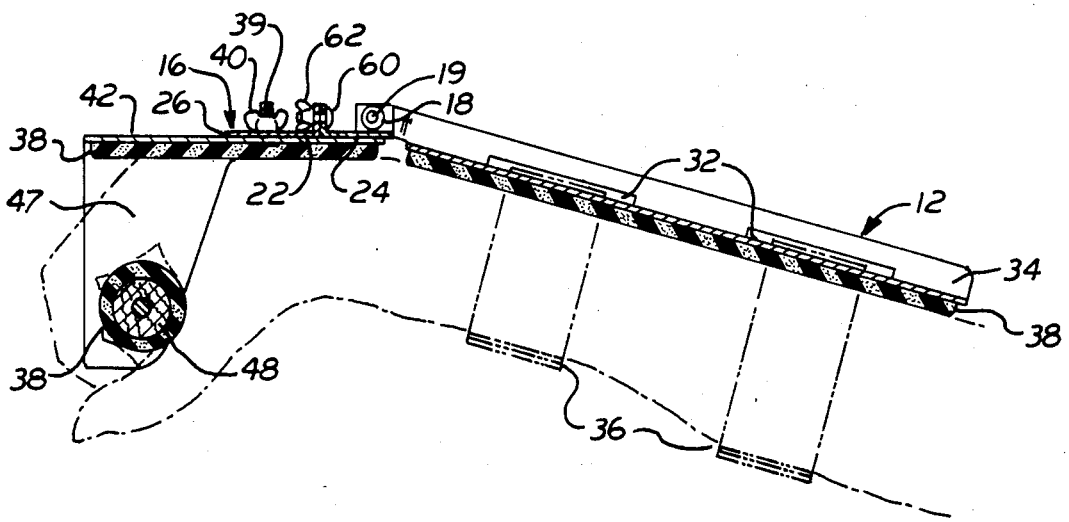
FIG. 2 is a cross-section in elevation along line 2—2 in FIG. 1 with a hand positioned in phantom.
Figure 3:
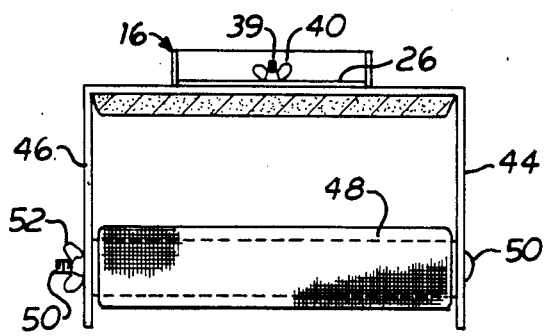
FIG. 3 is a front elevation view of the articulated hand splint in FIG. 6.
Figure 5:
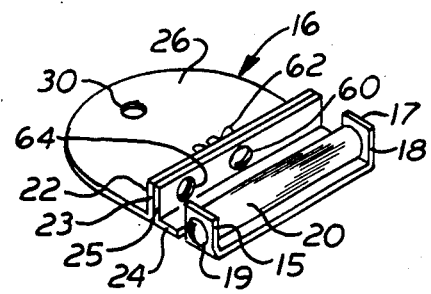
FIG. 5 is a perspective view of the transition bracket in the hand splint of FIG. 1.

The transition bracket 16 shown in detail in FIG. 5 comprises a U-shaped member 18 with arms 15 and 17 supported by an optional shaft 20, a pair of L-shaped members 22 and 24 with the upright arm of each, 23 and 25 respectively, parallel to the shaft 20. L-shaped member 24 is integral with U-shaped member 18. An oval-shaped plate 26 forms a bottom extension from the lower portion of L-shaped member 22. The oval-shaped plate 26 has an opening 30 near its center. Opening 30 is used to mount the transition bracket 16 to the hand grip housing 14 and by loosening the mounting to provide side to side movement of bracket 16 with respect to the hand grip housing 14.

Bolt 60 runs through the middle of upright arms 23 and 25 to hold them together with the assistance of wing nut 62. Loosening of wing nut 62 allows the housing 14 to rotate with respect to the arm support frame 12. Hole 64 through arms 23 and 25 is an optional item to provide for permanent bolting together of arms 23 and 25 if the rotating action is not needed.

A nut at the end of U-shaped bracket 18 together with bolt 19 through shaft 20 holds the U-shaped bracket 18 to the arm support frame 12. In the alternate embodiment of FIGS. 7-9, the bolt 19A does not run the length of bracket 18A. Nut 21 on each side holds the elements together. A loosening of the nut 21 and bolt 19A allows the arm support frame 12A to pivot up or down.

The arm support frame 12 also has two or more lateral holes 32 on each side between the base 33 and lip 34. A strap 36 made out of leather, nylon or webbing material is run through holes 32 and around the forearm to bind the forearm to the base 33 of arm support frame 12. Velcro is used to hold the ends of the strap 36 together.

Lamb's wool 38 is placed between the bottom portion of arm support frame 12 and the forearm to provide protection to the forearm. Plate 26 is affixed to hand grip housing 14 by way of nut 39 and wing nut 40. Loosening of nut 39 and wing nut 40 allows side to side movement of transition bracket 16 with respect to the hand grip housing 14.

The hand grip housing 14 comprises a top portion 42 and side portions 44 and 46 respectively. Sides 44 and 46 are held apart by a dowel 48 which is affixed to the sides 44 and 46, respectively by a bolt 50 and wing nut 52.

Figure 4:
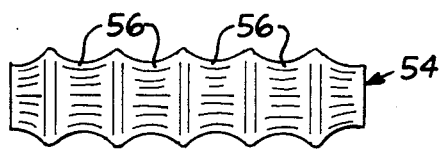
FIG. 4 is a plan view of an optional hand grip.

A finger mount pan 54 (FIG. 4) can be substituted for the dowel 48. This finger mount pan 54 has finger receptacles 56 so that the hand may rest fully in an extended position.

Figure 6:
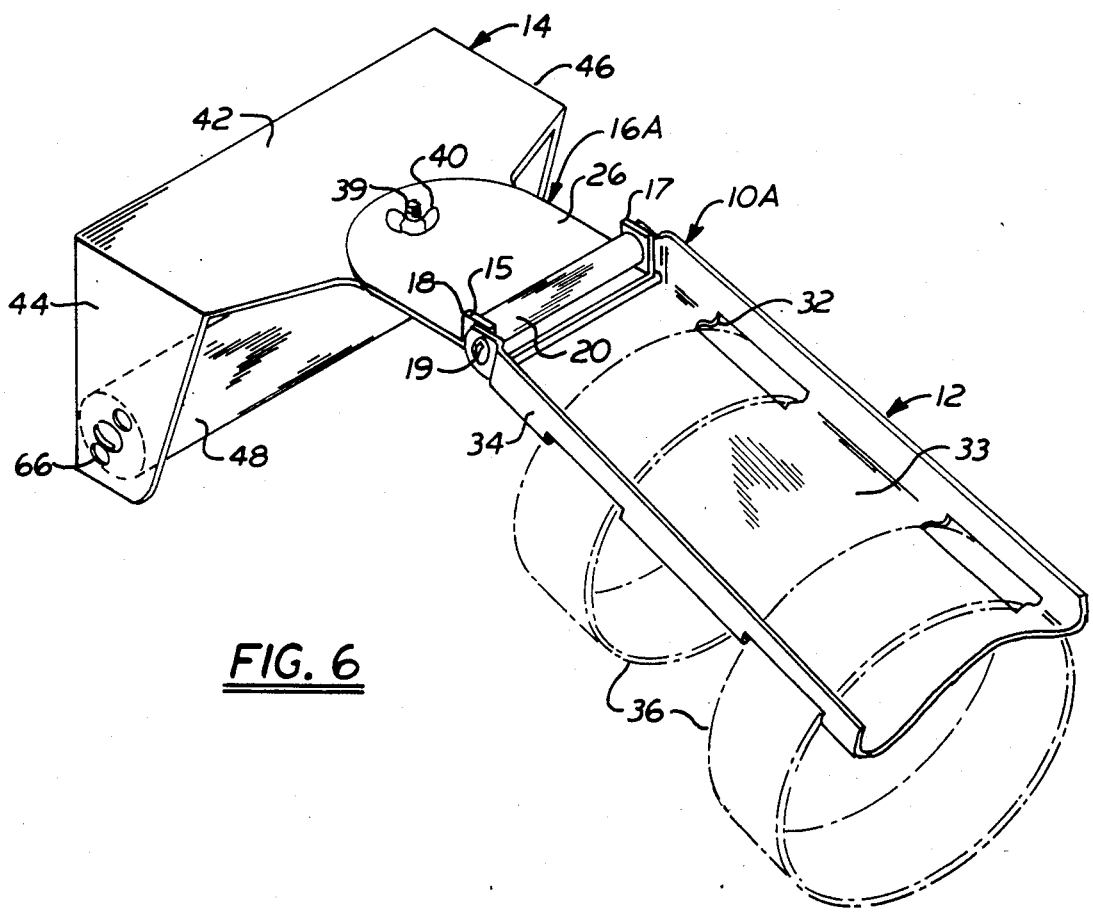
FIG. 6 is a perspective view of an alternate articulated hand splint movable in two directions.

FIG. 6 shows an optional articulated hand splint 10A, which differs from 10 only in that the transition bracket 16A is a single integral unit and does not have the L-shaped plates 22 and 24 respectively. Therefore arm support frame 12 moves up and down and the transition bracket 16 moves from side to side but there is no rotating of the device.

Lamb's wool 38 is also placed under the top 42 of the hand grip housing 14 so as to protect the top of the hand from the hand splint device. It is also applied around dowel 48 so that hand 47 is protected.

Figure 7:
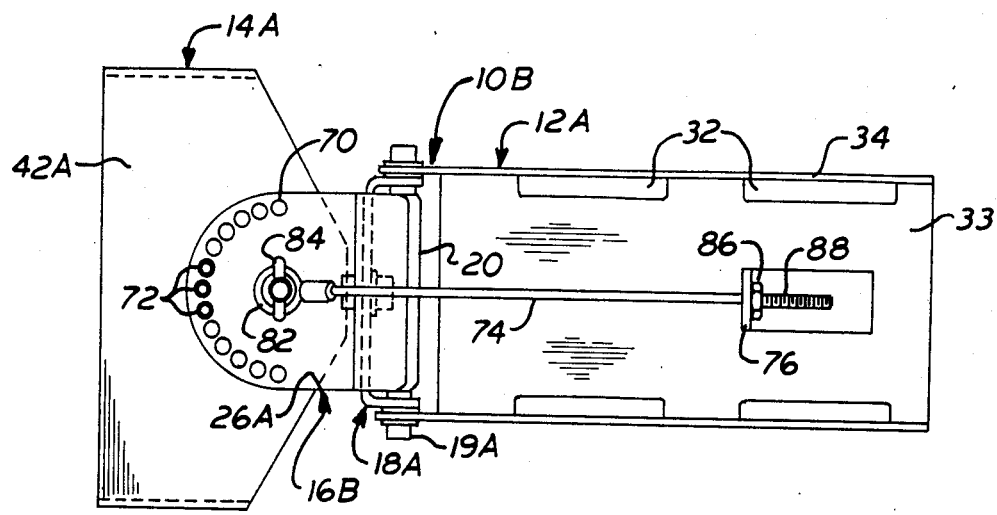
FIG. 7 is a plan view of another alternate articulated hand splint movable in two directions.
Figure 8:
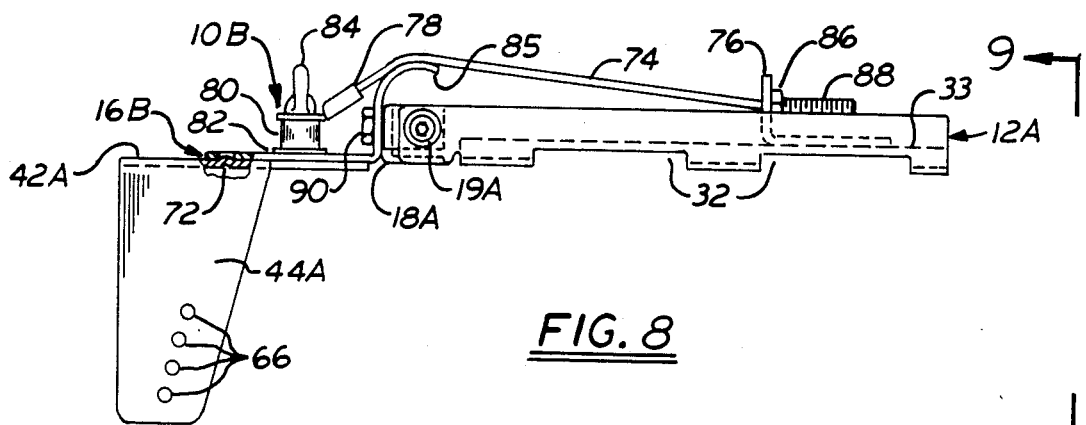
FIG. 8 is a side elevation view partially in section of the hand splint of FIG. 7.
Figure 9:
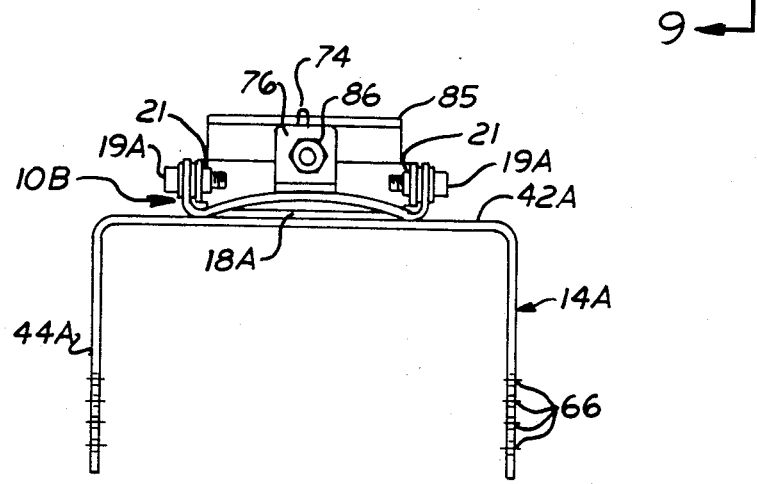
FIG. 9 is an end view in elevation of the hand splint of FIGS. 7 and 8.

FIGS. 7-9 show another optional articulated hand splint 10B differing from 10 in several ways. Hand splint 10B has a wire rope 74 adjusted for tension at one end by bolt 86 and screw 88. An L-shaped member 76 affixed to bottom 33 of arm support frame 12A by welding or rivets anchors this end of the wire rope 74. The other end is attached to eyelet 78 which in turn is attached to transition plate 16B by a wing nut with integral bolt 84, spacer 80 and washer 82. A projecting support member 85 integral with the base portion 26A of the transition plate 16B maintains the wire rope 74 at the proper height to strengthen hand grip housing 14A.

The transition plate 16B on splint 10B has a series of holes 70 on the edge of base portion 26A, each hole capable of fitting over a bump 72 in the top 42A of the hand splint housing 14A. The occupational therapist determines the proper angle for the housing 14A with respect to arm support frame 12A, places the bump 72 in the proper hole 70, tightens down on nut 84 and adjusts nut 86 for proper tension.

The U-shaped member 18A is bolted by bolt 90 to the upright support member 85 of the transition plate 16B. The arm support frame 12A can be moved up or down with respect to U-shaped member 18A by loosening bolt 19A.

An occupational therapist uses devices 10, 10A or 10B in anti-spasticity splinting for decorticate and decerebrate posturing. This is of special importance in use with patients having spasticity associated with brain trauma injuries. The pan 54 encourages or maintains the finger extension and thumb abduction while in the strapped position. The majority of pressure is placed on the dorsum of the hand rather than on the stiloid process of the wrist in order to help reduce or avoid development of pressure sores. The devices 10, 10A or 10B reduce further wrist and hand or finger flexion associated with spasticity, thereby helping to prevent the possibility for contracturers to develop. The splint can be easily removed periodically throughout the day at the therapist's discretion. Along with the correction of hand deflection the device also accommodates increased passive prom in the wrist and hand while allowing for easy monitoring of skin integrity.

The arm support frame 12, transition bracket 16 and hand grip housing 14 can be made of aluminum, steel or high strength plastic, such as polyurethane with a durometer hardness of 70 or more on the F scale. Preferably, the transition bracket is made of metal.

Having thus described the invention what is claimed and desired to be secured by Letters Patent is:

1. An articulated hand splint comprising an arm support frame having a first and second end and a hand grip housing connected together with a transition bracket having a first and second end and the bracket containing at least two pivot points for positioning a hand with respect to its forearm strapped to the arm support frame, the first end of the support frame connected to the first end of the transition bracket, the hand grip housing containing a top portion and two downwardly extending side walls with the two side walls connected together by a hand grip around which the fingers of a patient's hand are placed, the top portion of the hand grip housing being in parallel planes with and attached to but movable with respect to the second end of the transition bracket, the transition bracket having at the first end an elongated member with an extending arm at each end, the first end of the support frame attached to and pivoting on each extending arm, the support frame being strapped over the dorsal surface of a patient's forearm.

2. An articulated hand splint according to claim 1 wherein the hand grip is a dowel.

3. An articulated hand splint according to claim 1 wherein the hand grip is a finger mount pan.

4. An articulated hand splint according to claim 1 wherein the arm support frame comprises a base with parallel elongated edges on each side, the base being in contact with the top of a patient's forearm, a pair of upwardly projecting parallel lips from each elongated edge of the base and a hole between the lips and the base for receiving a strap to wrap around the forearm and thereby secure the forearm to the arm support frame.

5. An articulated hand splint according to claim 1 wherein lamb's wool is mounted between each surface of the splint and any contact point with a patient's skin.

6. An articulated hand splint according to claim 1 wherein there are three pivot points on the transition bracket.

7. An articulated hand splint according to claim 1 wherein the transition bracket second end is an oval shaped plate.

8. An articulated hand splint according to claim 4 having a wire rope attached at a first end to the transition bracket and at a second end to the base of the arm support frame.

9. Method of treating hand spasticity in a brain damaged patient comprising strapping an arm support frame having a first and second end top the dorsal surface of the patient's forearm and engaging the patient's hand on a hand grip in a housing, the frame and housing connected together with a transition bracket having a first and second end and the bracket containing at least two pivot points employed to position the hand with respect to the forearm, the first end of the support frame connected to the first end of the transition bracket, the hand grip housing containing a to portion and two downwardly extending side walls with the side walls connected together by a hand grip around which the fingers of the patient's hands are placed, the top portion of the hand grip housing being in parallel planes with and attached to but movable with respect to the second end of the transition bracket having at the first end and an elongated member with an extending arm at each end, the first end of the support frame attached to and pivoting on each extending arm.

* * * * *

UNITED STATES PATENT AND TRADEMARK OFFICE
CERTIFICATE OF CORRECTION

PATENT NO. : 4,660,550
DATED : April 28, 1987
INVENTOR(S) : Rudolph H. Bodine

It is certified that error appears in the above-identified patent and that said Letters Patent is hereby corrected as shown below:

Column 4, Claim 9, line 41, "top" should read -- to --;
line 49, "to" should read -- top --;
line 55, delete "and".

Signed and Sealed this

Twenty-seventh Day of October, 1987

Attest:

DONALD J. QUIGG

Attesting Officer

Commissioner of Patents and Trademarks